(12) United States Patent
Olive et al.

(10) Patent No.: US 7,004,109 B2
(45) Date of Patent: Feb. 28, 2006

(54) AQUACULTURE OF MARINE WORMS

(75) Inventors: Peter James William Olive, Tyne and Weir (GB); Stephen Craig, Newcastle upon Tyne (GB); Peter Brian Douglas Cowin, Hampden, ME (US)

(73) Assignee: Seabait Limited, Northumberland (GB)

( * ) Notice: Subject to any disclaimer, the term of this patent is extended or adjusted under 35 U.S.C. 154(b) by 0 days.

(21) Appl. No.: 10/483,314

(22) PCT Filed: Jul. 1, 2002

(86) PCT No.: PCT/GB02/03021

§ 371 (c)(1),
(2), (4) Date: Jan. 9, 2004

(87) PCT Pub. No.: WO03/007701

PCT Pub. Date: Jan. 30, 2003

(65) Prior Publication Data

US 2004/0159288 A1  Aug. 19, 2004

(30) Foreign Application Priority Data

Jul. 14, 2001 (GB) .................................. 0117257

(51) Int. Cl.
*A01K 29/00* (2006.01)
(52) U.S. Cl. ........................................................ 119/6.7
(58) Field of Classification Search .............. 119/6.7, 119/270, 6.5, 6.6; 426/1; 43/55
See application file for complete search history.

(56) References Cited

U.S. PATENT DOCUMENTS

| | | | |
|---|---|---|---|
| 3,566,636 A * | 3/1971 | Elfert | 70/276 |
| 3,889,638 A * | 6/1975 | Riley | 119/6.7 |
| 3,961,603 A * | 6/1976 | Gaddie, Sr. | 119/6.7 |
| 4,055,911 A * | 11/1977 | Aylor | 43/55 |
| 4,148,154 A * | 4/1979 | King | 47/66.6 |
| 4,161,158 A * | 7/1979 | Kartesz | 119/6.7 |
| 4,192,254 A * | 3/1980 | Apel | 119/6.7 |
| 4,417,545 A * | 11/1983 | Finney | 119/6.6 |
| 4,513,685 A * | 4/1985 | Frijters et al. | 119/6.7 |
| 4,815,416 A * | 3/1989 | Wolff | 119/6.7 |
| 5,042,427 A * | 8/1991 | Bedding | 119/6.7 |
| 5,664,366 A * | 9/1997 | Lopuszanski et al. | 43/55 |
| 5,924,238 A * | 7/1999 | Yanohara | 47/1.01 F |
| 6,193,902 B1 * | 2/2001 | Eguchi | 252/1 |
| 6,223,687 B1 * | 5/2001 | Windle | 119/6.7 |
| 6,240,876 B1 * | 6/2001 | Giannaris | 119/6.7 |
| 6,360,688 B1 * | 3/2002 | Olive | 119/6.7 |
| 6,572,877 B1 * | 6/2003 | Gergely et al. | 424/442 |

FOREIGN PATENT DOCUMENTS

| | | | |
|---|---|---|---|
| FR | 2737083 A1 | | 1/1997 |
| JP | 52069796 A | * | 6/1977 |
| JP | 357150350 A | * | 9/1982 |
| JP | 59169455 A | * | 9/1984 |
| JP | 407308138 A | * | 11/1995 |

(Continued)

*Primary Examiner*—Yvonne R. Abbott
(74) *Attorney, Agent, or Firm*—Drinker Biddle & Reath LLP

(57) ABSTRACT

The present invention provides a method for the aquaculture of marine deposit feeders, such as *Arenicola marina* and *Arenicola defodiens*. The method includes providing a foodstuff such as brewery yeast or waste from fish farms within the substrate housing the worms. The foodstuff is conveniently particulate or microparticulate to aid intimate admixture with a substrate, which is typically sand.

17 Claims, 8 Drawing Sheets

FOREIGN PATENT DOCUMENTS

| RU | 2054402 C1 | 2/1996 |
| WO | WO93/10060 A1 | 5/1993 |
| WO | WO94/19296 A1 | 9/1994 |
| WO | WO00/32540 A1 | 6/2000 |

* cited by examiner

AQUACULTURE OF MARINE WORMS

The present invention relates to the aquaculture of marine worms.

Marine bait worms are animals in the Class Polychaeta of the *Phylum Annelida* or in the *Phylum Sipunculida* or are other such animals as may be generally referred to as worms which may be used as bait by anglers. Such worms are also used as foodstuffs for fish, crustaceans and other organisms, for toxicity testing and for other scientific purposes.

Naturally occurring supplies of marine worms are not inexhaustible and collection of marine worms has been recognised as a cause of serious environmental concern.

Aquaculture of marine worms provides a sustainable source.

Methods of enhancing the aquaculture of polychaete worms are described in WO-A-98/06255 and WO-A-98/44789. WO-A-98/06255 describes the use of cryopreservation techniques and also the manipulation of the photoperiod to control the time of sexual maturity of marine worms. WO-A-98/44789 describes controlling the photoperiod to enhance the growth of polychaete worms belonging to the *Nereidae* or *Eunicidae* families, typically the ragworm *Nereis virens*.

In nature, there are a number of polychaete worms, which have attracted the attention of the aquaculture industry and sea anglers. Among these the *Arenicolidae* (lugworms) are particularly important (Gambi et al, 1994; Olive, 1993). At the same time there have been concerns that bait digging for these animals may cause environmental damage (Olive, 1993) and studies to initiate large-scale culture have begun. The culture of these animals could potentially provide another source of polychaete materials for use in the aquaculture industry.

*Arenicola marina* (lugworm) is an iteroparous animal, breeding several times per lifetime but at annual intervals (Clark and Olive, 1973). The feeding behaviour is also very different from that of the ragworm *Nereis virens*. *A. marina* is a typical marine deposit feeder (Jumars, 1993; Fauchald and Jumars, 1979). The animals live in J-shaped burrows and feed by ingesting sand grains or other substrate at the head of the horizontal section of the burrow (Wells 1949). This feeding activity may cause downward movement of sand from the surface of the beach (or sediment) causing a depression at the sand surface and forming a head shaft giving the feeding structure a U shaped configuration with an open J shaped gallery and tail shaft and a sand filled head shaft. The animal respires by driving water from the tail shaft forwards through the gallery and through the sand in the region of the head shaft. This respiratory movement of water may additionally enrich the sand in the region of the base of the head shaft where feeding occurs. From time to time the animal moves from the gallery backwards through the tail shaft to produce casts of defeacated sand or substrate at the surface. Although, *A. marina* ingests sediment in a non-selective way, selective feeding in the field has been observed in some closely related species (Hylleberg, 1975) and there is indirect evidence for it in *A. marina*. Hylleberg (1975) thought that meiofauna were the main source of food but that the worms also benefited from the direct uptake of nutrients. Cadee (1976) and Rijken (1979) suggested that diatoms were important food items. However several researchers have made observations that the worms accumulated bacteria and that this forms a substantial part of the diet (Boon et al., 1978; Rijken, 1979; Grossman and Reichardt, 1991).

To date, the only published reference to the aquaculture of lugworms is described by D'Asaro et al. in "Lugworm Aquaculture", Report Number 16, State University System of Florida, Sea Grant College Program, September 1976 (FLA Reg. 3:331/16/976). In the proposed hatchery, the recommended food for lugworms (see page 16) is described as seagrasses. Four such seagrasses were trialled, namely turtle grass (*Thalassia testudinum*), manatee grass (*Syringodium fillforme*), shoal grass (*Diplanthera wrightii*) and widgeon grass (*Ruppia maritima*). A variety of other foodstuffs were also trialled (see Table III, page 74) but were not found to be satisfactory. In fact D'Asaro concluded that the food provided must be in a form which will gradually decompose and will not contribute to immediate environment degradation, these requirements limiting the suitability of a number of foodstuffs. In the regime proposed by D'Asaro et al, the seagrass was dried, milled to a particle size of less than 700 $\mu$m and then mixed with sea water before being sprayed as a slurry onto the rearing area for the worms. Allowing the seagrass to soak in seawater for at least one hour ensured that the slurry sank immediately upon application forming a layer on the top of the substrate in which the worms had formed their tubes.

However, despite the detail reported by D'Asaro, no commercial farming of lugworms currently takes place.

We have now produced an improved method of farming lugworms.

The present invention provides a method for the aquaculture of deposit feeding marine worms (such as lugworms of the genus *Arenicola*), said method comprising providing a foodstuff within the substrate housing the worms.

Preferred species of lugworms suitable for use in the method described are members of the family *Arenicolidae*, in particular *Arenicola marina* and *Arenicola defodiens*.

The substrate housing the worms may be intimately admixed with the foodstuff (which will be organic matter, for example may be any form of organic matter that may be easily admixed with the substrate, and which as in the examples described herein may be a yeast obtained as a by-product of brewing, or an organic slurry derived from a fish farm effluent) and this approach is preferred when the bed of substrate is being prepared prior to the introduction of the worms or their larvae. However, all that is required to obtain the benefit of improved growth characteristics is that the foodstuff is not left as an exposed layer on top of the substrate, but is located within the substrate itself. To aid intimate admixture of the foodstuff and the substrate, the foodstuff is conveniently in particulate or microparticulate form, that is the foodstuff is of a similar or smaller particle size to that of the substrate itself.

During growth of the worms it may be desirable to replenish the levels of foodstuffs provided for the worms. Whilst it is possible to replace the original substrate/foodstuff admixture with a new admixture, this would entail disturbing the worms and moreover would be labour intensive and costly to conduct on a commercial scale.

A more advantageous way of replenishing the foodstuff is simply to add a layer of the selected foodstuff onto the original substrate and to cover the layer of additional foodstuff with a further layer of a secondary substrate. Alternatively a solution or dispersion (slurry) of the foodstuff could be introduced under pressure into the substrate, care being taken not to unduly disturb the worms in their tubes.

Any suitable particulate substrate may be used to house the worms. Typically a sandy substrate is suitable, but other substrates comprising particles of similar size (eg glass beads) could also be used. Sand is preferred due to its wide availability and low cost.

A suitable depth of substrate is provided to house the worms and to enable them to produce the tubes in which they live. A depth of approximately 5 cm of substrate could be provided initially, although a greater depth is also possible, with mature lugworms forming tubes at depths of 20 to 40 cm in their native habitats. For ease of harvesting the worms however it is desirable to use the minimum depth of substrate. Where additional foodstuff is to be provided by introduction into the substrate in the form of a suspension or dispersion a greater initial layer of substrate may be advantageous since this may provide a zone within the substrate into which the foodstuff can be introduced without disturbing the lugworms. Where this method of introducing additional foodstuff is to be adopted, the foodstuff may be introduced from the top of the substrate or from the bottom of the substrate. Optionally pipes provided with multiple fine nozzles may be pre-laid so that the solution/dispersion of foodstuff may be jetted into the substrate.

In an alternative embodiment, a layer of foodstuff and a layer of secondary substrate may be provided on the top of the initial substrate layer. Alternatively, a layer of foodstuff can be mixed with the upper layers of the initial substrate before the introduction of the secondary substrate.

Thus, after a predetermined period of time (which may vary depending upon the food:substrate ratio in the admixture initially provided as well as the size and density of the worms) a further layer of foodstuff may be located onto the initial substrate layer and then covered with a further layer (typically of a depth of 4 to 10 cm) of a secondary substrate. This process may be repeated using further layers of foodstuffs and tertiary or further layers of substrate. The secondary, tertiary or further substrates may be the same or different to each other or to the initial substrate. Generally, the secondary substrate layer and any other further substrate layer will be of similar depths (typically 4 to 10 cm), but this is not essential. Sand is the preferred substrate for each substrate layer used. Any foodstuff comprising organic matter can be used in the present invention, including foodstuffs of marine origin. However, a real problem recognised in the aquaculture industry is its dependence on raw materials (feeds) that have derived from fishing or marine materials. A much preferred form of foodstuff therefore is foodstuffs derived from non-marine sources or the slurry that may be recovered from farms (for example pig, chicken or cattle farms or fish farms). Of particular interest is the slurry recovered from fish farms using recirculation procedures or the faeces or other waste products recovered from fish farms. Also of interest is the bacteria-containing slurry recovered from a recirculation filter, biofilter or bioreactor. Again, the slurry from the recirculation filter, biofilter or bioreactor of fish farms is of particular interest, but the invention is not limited to this alone.

Many marine animals require essential fatty acids (long chain unsaturated fatty acids) not present in non-marine sources or from by-products of fish farming such as the slurry that may be recovered from fish farms using recirculation procedures or the faeces and other waste products recovered from fish farms.

Consequently it is recognised that shrimps, fish and other marine animals require marine based foodstuffs to grow successfully (See, for example, Porteres, 1991 in Comp. Biochem. Physiol Vol 100A, No. 1, pages 211–215). This dependence of aquaculture on marine food sources is widely believed to lead to depletion of the marine environment by the aquaculture industry, a problem of grave international concern as discussed by Naylor et al in "Effect of Aquaculture on world fishery supplies" Nature (2000) 405:1017–1024 and also in the American Association for the Advancement of science meeting held 18 Feb. 2001 entitled "The Aquaculture Paradox—Does Fish Farming Supplement or Deplete World Fisheries".

We have now found, however, that as a consequence of the process described herein, lugworms are able to accumulate the long chain unsaturated fatty acids essential to other commercially important marine animals from other sources, in particular from non-marine derived foodstuffs, that need not include those long chain unsaturated fatty acids. Consequently the process described herein, when utilising non-marine based foodstuffs, or by-products and waste products recovered from fish farms, offers a real solution to the problem of depletion of the marine environment through aquaculture.

In a first embodiment of the invention a preferred foodstuff for use in the method described is yeast, preferably brewer's yeast (also termed "brewery yeast"). A convenient source of such foodstuff is the waste (spent) yeast obtainable as a by-product from a brewery or distillery.

In a second embodiment of the invention a preferred foodstuff for use may be a bacteria rich slurry recovered from a fish-farm using recirculation systems and bioreactors to remove waste organic material such as faeces and dissolved organic matter, or a slurry containing the waste faeces recovered from a fish farm. We have found that such slurry typically consists of 80% water and 20% organic matter and can be used directly. It would however be possible to remove some or all of the water prior to use.

In a third embodiment of the invention the preferred foodstuff may be a mixture of yeast and the bacteria rich slurry as in the first and second embodiments combined and in the third embodiment the overall growth rates of the cultured worms in the longer term may be superior.

Other similar sources of foodstuffs may be contemplated, for example any algae or micro-organisms, and indeed other sources of foodstuff are also possible.

Typically, using brewer's yeast, lugworms produce the following fatty acids: C16:1n7, C18:1n12, C18:1n7, C18:2n6, C18:2n3, C18:3n3, C20:0, C20:1n9, C20:2n6, C20:4n6, C20:5n3, C22:2n3, C22:6n6, C22:6n3. It is of considerable interest that the food substance brewery yeast contained only the following fatty acids C16:0, C22:0, C25:0, C26:0, C27:0, C28:0, C29:0, C30:0 and C31:0 all of which are saturated long chain fatty acids at a concentration greater than 0.4 mg $g^{-1}$ dry weight. The only unsaturated fatty acid found to be present was C18:1n9 and this was present only in trace amounts at a concentration of 0.08 mg $g^{-1}$ dry weight. We conclude therefore that net synthesis of unsaturated fatty acids occurs in the system and that there is a net accumulation of these unsaturated fatty acids within the body tissues of the lugworms.

The lugworms farmed may be of any size, depending upon the end use. Generally however, lugworms of 5 to 6 g are of a commercially useful size and may be used for fishing or for food, especially aquaculture food. With the methodology described above a 0.5 g lugworm may grow to a 5–6 g size within 90 to 120 days.

Any density of worms may be used. We have found, however, that a density of 100 to 300 worms per square metre gives good results with embodiments 1 and 2 but that in embodiment 3 higher densities up to 1000 worms per square metre may be used according to the depth of the substrate/foodstuff mixture and that the growth rate of individual worms may be greater at these higher densities. The present invention will now be further described with reference to the figures which illustrate different exemplary methods of introducing foodstuff into the substrate for lugworm farming.

FIG. 1 illustrates an exemplary method of creating a foodstuff/substrate mixture ready for addition of lugworms for farming. A rotating stirring apparatus illustrated generally at (1) and moving in the direction of arrow (2) is used to mix foodstuff into a substrate (4), such as sand. A commercially available garden rotivator or similar instrument may be used for this purpose. As illustrated, the bed is partially enriched with foodstuff, with a foodstuff/substrate mixture being shown at (3) and a clean substrate at (4). Arrows (5) indicate the addition of the foodstuff. In this example the foodstuff is spent brewer's yeast used directly as received from the brewery but may also be brewer's yeast in particulate (dried) form or a slurry recovered from a fish farm. Once a foodstuff/substrate mixture (3) has been produced in the whole bed the lugworms can be added to the bed for farming as indicated generally by arrow A. A layer of sea water will be delivered to cover the substrate/food mixture (3) to provide suitable conditions for the growth of marine worms, providing oxygen and removing waste products. The sea water may be delivered constantly, may be subject to prior filtration to remove competing organisms, may be treated using various commercially available recirculation systems or may be used once and disposed of. The sea water may be of any suitable temperature for the growth of marine worms but may preferably be sea water obtained from a power station or other source that has been heated and which may be mixed with sea water at ambient temperatures to maintain an optimum temperature for growth which in the case that the worms are *Arenicola marina* or *Arenicola defodiens* will be a temperature in the range 12 to 20° C. The supply of sea water may also be intermittent to allow for drainage of the substrate/sand mixture as may occur naturally in the intertidal environment in which these animals are found in nature.

The temperature of the sea water may be adjusted to regulate the maturation and spawning of lugworms according to known data.

FIG. 2 illustrates lugworms (6) shown in situ in a foodstuff/substrate mixture (3). In this illustration the lugworms (6) have created their housing tubes (7) and have been growing in the foodstuff/substrate mixture (3) for some time. In this embodiment, additional foodstuff is shown being introduced in the form of a suspension or solution via pipes (8) located in the lower layer of the foodstuff/substrate mixture (3). The arrows indicate the movement of the additional foodstuff suspension/solution sideways into the substrate mixture (3).

FIG. 3 again illustrates lugworms (6) located in housing tubes (7) within a foodstuff/substrate mixture (3). As in FIG. 2 the lugworms have been growing for some period of time, such that additional foodstuff is now required to sustain their growth. In this embodiment additional particulate foodstuff is incorporated as a layer on the top of the original substrate (3) as shown generally be arrow B and is admixed into the top zone thereof using a stirring apparatus (1). A secondary layer of substrate (9) may be added as the stirring apparatus (1) moves across the worm bed.

In FIG. 4 the lugworms (6) are again already settled into an original foodstuff/substrate mixture (3) and further foodstuff (10) is added by means of a hollow plough (11) which is dragged through an upper layer of the foodstuff/substrate mixture (3). The vibration of the plough (11) drives the worms (6) down into their housing tubes (7) within the original substrate (3). Optionally a chain (12) is included to enhance this effect. The additional foodstuff is jetted into the original foodstuff/substrate mixture (3) and is admixed therewith during the action of ploughing. In very large systems the admixture of food with the substrate may be achieved by application of the venturi principle achieved by pumping a mixture of sea water and substrate (e.g. sea water and sand) past an inlet through which is drawn in and mixed with the sea water and sand a fluid mixture of sea water and the food material (e.g. sea water and brewery yeast or fish farm effluent slurry, or similar suitable food material obtainable in bulk).

EXAMPLES

Example 1

Small lugworms with an average weight of 0.6 g were introduced to a sand substrate at a numerical density of 150 individual per square metre in suitable tanks where the sand had a depth of 15 cm. It is also possible to introduce the lugworms at densities at least twice this numerical density and obtain similar results.

Figure 1:
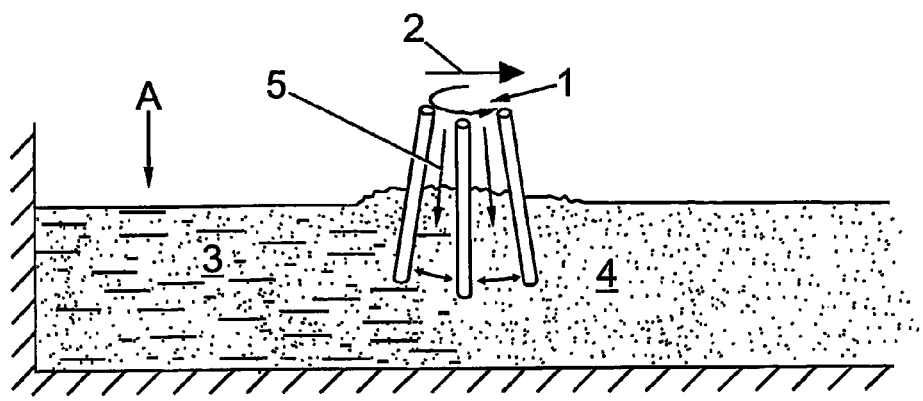

The animals were fed according to the invention by mixing brewers yeast waste in liquid form with the sand substrate in a number of ways:

Treatment 1: The yeast, at a ratio of 10 litres of brewers yeast per square metre, was thoroughly mixed with the sand substrate mechanically, as illustrated in FIG. 1, before the introduction of the worms. After 28 days, and at 28 day intervals thereafter, the worms were removed and the process of mixing the yeast with the sand was repeated and the worms re-introduced to the surface of the substrate into which they readily burrowed.

Figure 2:
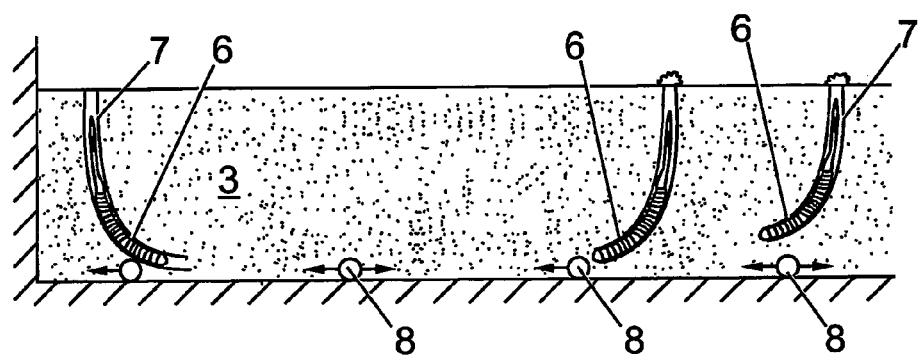

Treatment 2: The worms were introduced to sand in suitable tanks in which pipes had been placed as illustrated in FIG. 2. Brewers yeast was introduced to the sand at a ration of 10 Litres of brewers yeast in liquid form per metre square through the pipes in the sand. The yeast was delivered to the sand at 21 day intervals and the worms were not removed from the substrate until day 90 of the treatment.

Treatment 3: The worms were introduced to sand in suitable tanks in which pipes had been placed as illustrated in FIG. 2. Brewers yeast was introduced to the sand at a ration of 1 Litre of brewers yeast in liquid form per square metre through the pipes in the sand. The yeast was delivered to the sand at 28 day intervals and the worms were not removed from the substrate until day 90 of the treatment.

Table 1 provides data on the survival and growth rate of the worms in the three treatments.

TABLE 1

| | Numerical density $m^{-2}$ | Weight g replicate 1 | Weight g replicate 2 | Weight g replicate 3 | Mean Weight (g) | st deviation |
|---|---|---|---|---|---|---|
| Start | | | | | | |
| Treatment 1 - 28 day repeat mix | 150 | 0.780 | 0.713 | 0.687 | 0.727 | 0.048 |
| Treatment 2 - 21 day bottom feed | 150 | 0.507 | 0.413 | 0.593 | 0.504 | 0.090 |
| Treatment 3 - 28 day bottom feed | 150 | 0.567 | 0.533 | 0.587 | 0.562 | 0.027 |
| 90 Days | | | | | | |
| Treatment 1 - 28 day repeat mix | 133 | 8.539 | 7.157 | 6.514 | 7.404 | 1.035 |
| Treatment 2 - 21 day bottom feed | 105 | 6.154 | 5.820 | 5.511 | 5.829 | 0.322 |
| Treatment 3 - 28 day bottom feed | 133 | 3.525 | 7.329 | 5.486 | 5.446 | 1.902 |

Figure 5:
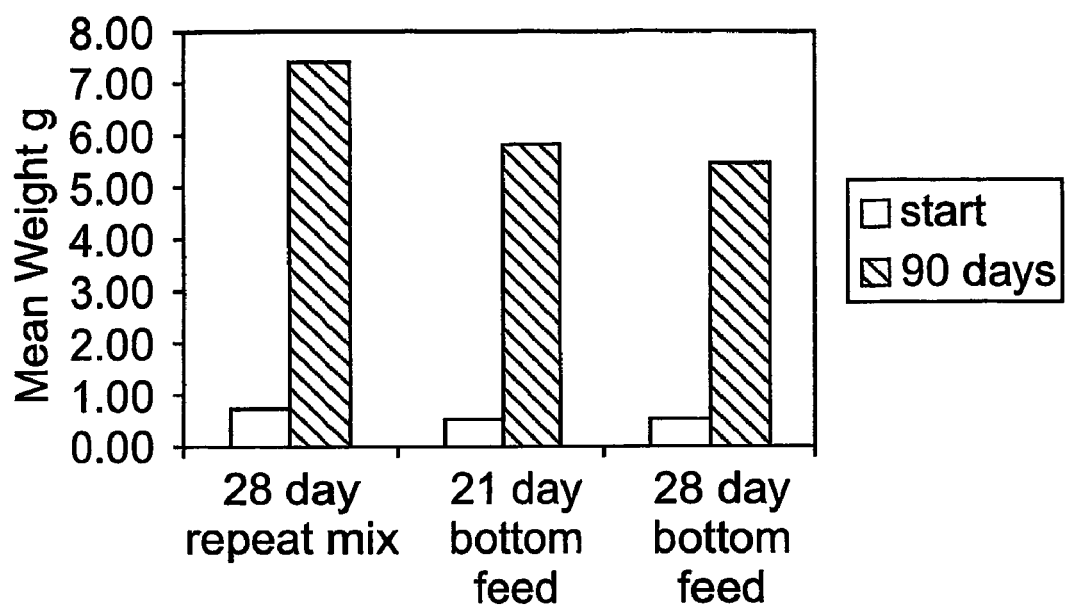
FIG. 5 shows the weight of lugworms at the start of feeding and after 90 days.

The growth of the lugworms in the three treatments is also illustrated in FIG. 5 showing the average size of the animals in each treatment at the start of the treatment and after a period of 90 days.

Example 2

In a further embodiment of the invention small lugworms were stocked into a sand substrate with an admixture of yeast as illustrated in FIG. 1 at three different densities and control worms of the same size were stocked into a similar sand at the same initial size and at the same density but without the addition of food.

Figure 6:
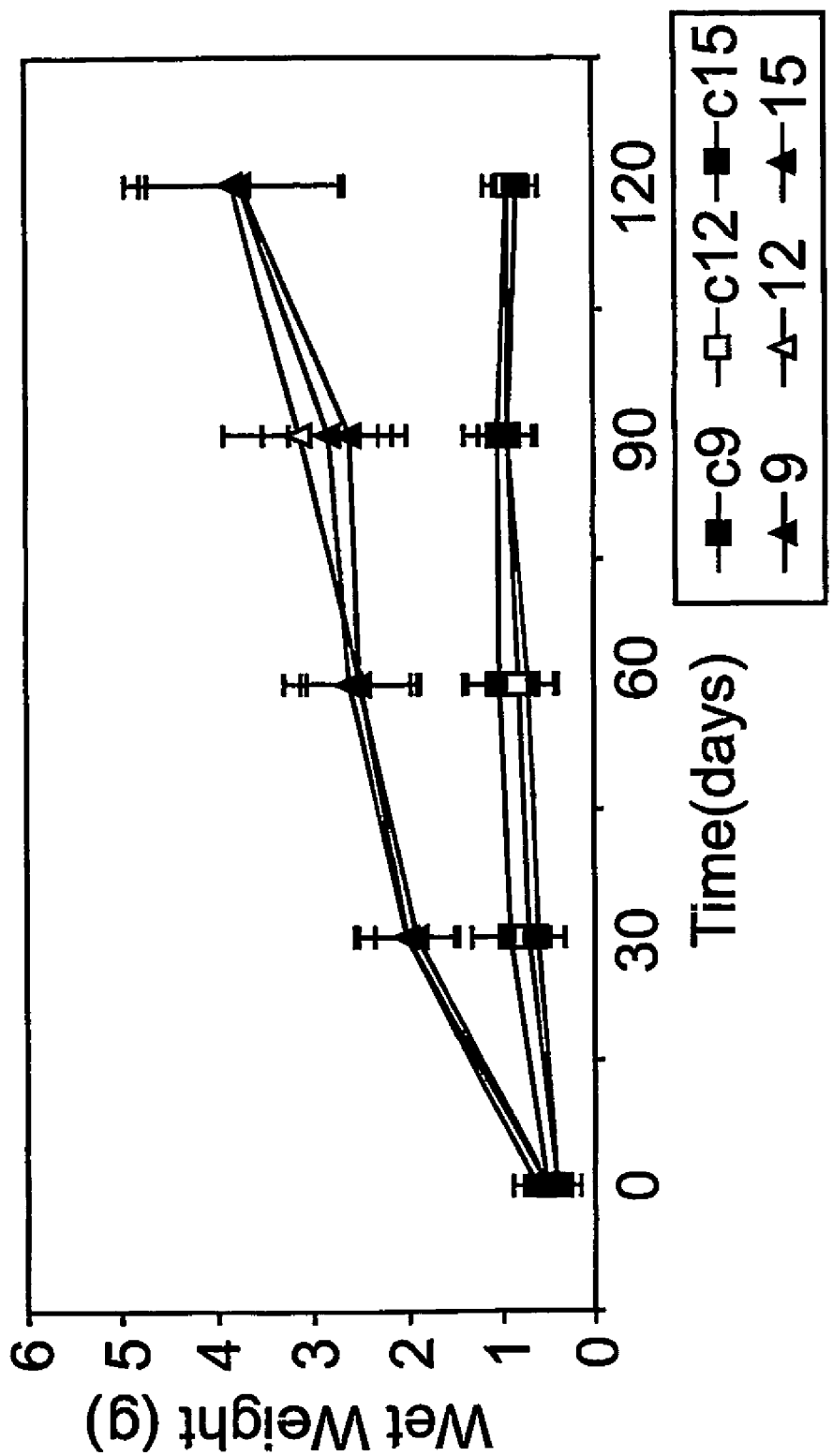
FIG. 6 shows the growth of *Arenicola marina* grown at different densities (90, 120, 150 per m$^2$) either unfed control (c) or fed.

The data illustrated in FIG. 6 show that the added food is the principle component of the system that allows for the substantial growth of the lugworm and is the source of the biomass.

Example 3

Figure 3:
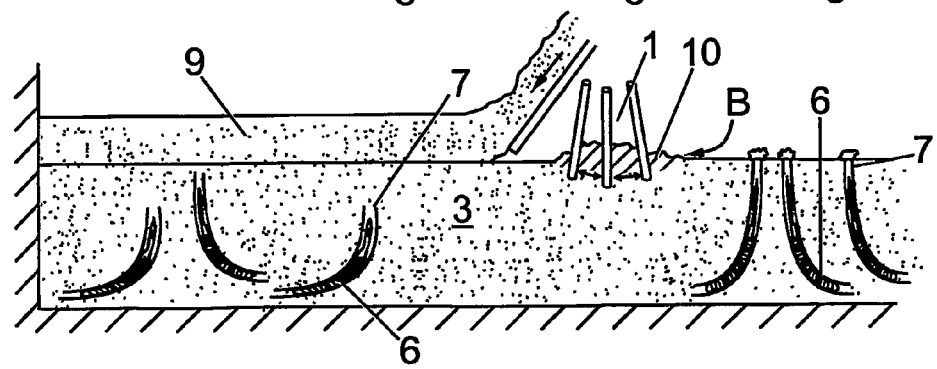
Figure 4:
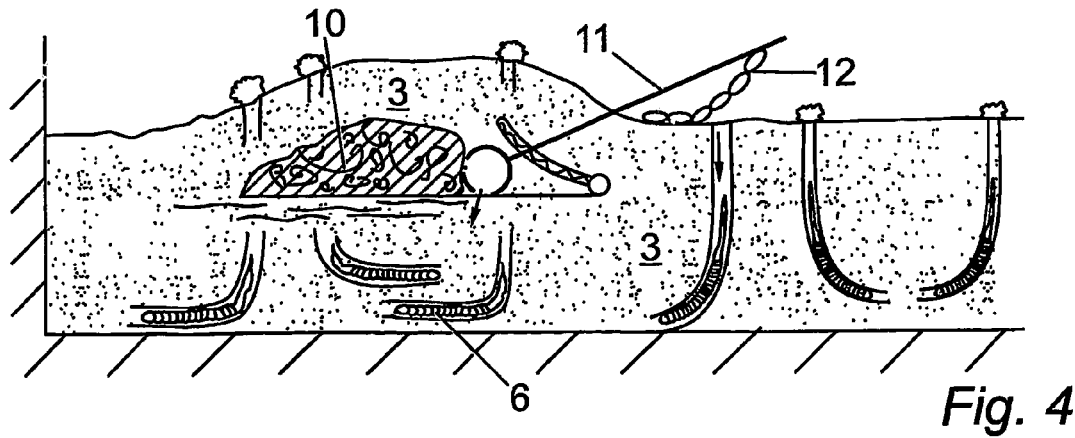

A further embodiment of the invention shows growth rates obtained using the method illustrated in FIG. 3.

In this embodiment the young animals were introduced to a sand substrate and food added by three methods.

Control Group: small worms were introduced into a sand substrate into which brewers yeast was introduced using the method illustrated in FIG. 1 with a further admixture of yeast to the sand as detailed in Treatment 1 above over 28 days.

Treatment Group 1000: small worms were introduced to a sand brewers yeast mixture as in Treatment 1 of Example 1. After a period of 28 days, and each 28 days thereafter, a further addition of brewers yeast was made using the procedure illustrated in FIG. 3. Yeast was added at a rate of 10 Litres $m^{-2}$ and the yeast was subsequently incorporated into the substrate by the further addition of sand to a depth of approximately 5 cm on each occasion when yeast was added.

Treatment Group 500: small worms were introduced to a sand brewers yeast mixture as in Treatment 1 of Example 1. After a period of 28 days, and each 28 days thereafter, a further addition of brewers yeast was made using the procedure illustrated in FIG. 3. Yeast was added added at a rate of 5 Litres $m^{-2}$ and the yeast was subsequently incorporated into the substrate by the further addition of sand to a depth of approximately 5 cm on each occasion when yeast was added.

Figure 7:
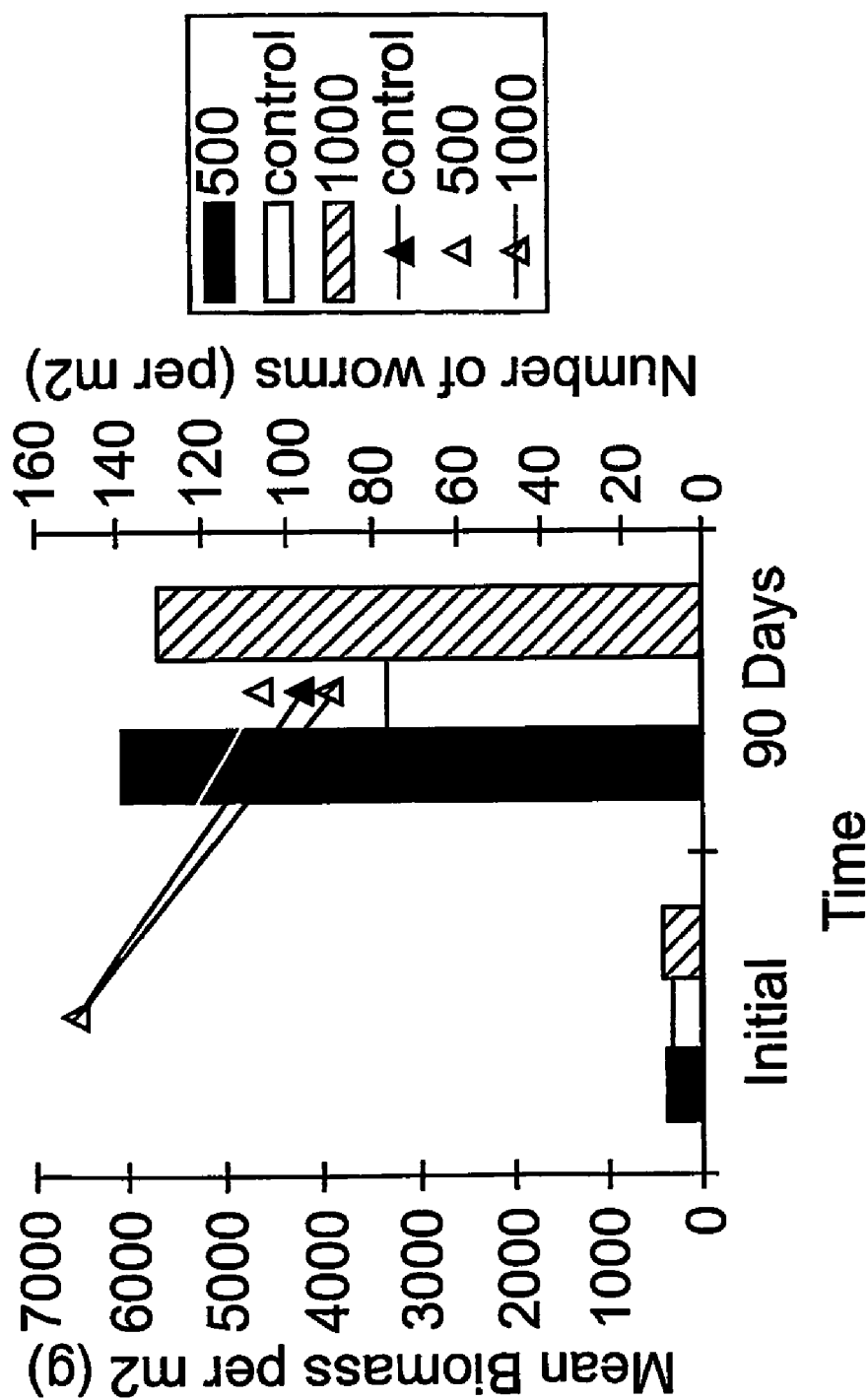
FIG. 7 shows the mean biomass and number of worms per m$^2$ fed yeast (rate 5000 ml and 10000 ml m$^{-2}$ respectively) covered with 5 cm layer of sand every 28 days according to the method illustrated in FIG. 3.

In each case small worms were introduced at a numerical density of 150 worms m $^2$. FIG. 7 shows the biomass and number of worms $m^{-2}$ intially and after a period of 90 days.

The mean weight of individual worms in the three treatments are shown in Table 2.

TABLE 2

| Treatment | Initial weight g | Final mean weight g | Standard deviation |
|---|---|---|---|
| 10 L $m^{-2}$ | 0.3 | 6.3 | 0.14 |
| Control (Treatment 1) | 0.2 | 5.3 | 0.15 |
| 5 L $m^{-2}$ | 0.2 | 5.6 | 0.11 |

Example 4

In this embodiment of the invention small lugworms obtained by breeding from worms that had been produced and reared as described within this Application were stocked into a previously used sand that had been enriched with 1) an admixture of brewer's yeast or 2) an admixture of a slurry recovered from a recirculation fish farm. The control animals were not provided with any additional food. Three replicates of each treatment were established and monitored. The initial weight of the animals was less than 1 g and in each case the initial stocking density was 150 worms per square metre. The food was replenished according to the method shown in FIG. 1 after 28 days. Table 3 shows the growth of the animals in these three treatments. This example illustrates the ability of the worms in the control group to recover organic matter already present in a previously used sand substrate, nevertheless the additional enrichment of the sand with brewery yeast or fish farm by-product significantly increases the growth rate and biomass of the worms.

into a previously used sand that had been enriched with 1) an admixture of brewer's yeast, 2) an admixture of a slurry recovered from a recirculation fish farm and 3) a combination of brewer's yeast and slurry recovered from a recirculation fish farm. The control animals were not provided with any additional food. Three replicates of each treatment were established and monitored. The initial mean weight of the animals was approximately 1 g and in each case the initial stocking density was 200 worms per square metre. The food was replenished according to the method shown in FIG. 1 after 28 days. Table 4 shows the growth of the animals in these three treatments. This example again illustrates the ability of the worms in the control group to recover organic

TABLE 3

| | FOOD STUFF | | | | | |
|---|---|---|---|---|---|---|
| | CONTROL | | BREWERY YEAST | | FISH WASTE | |
| | | | TIME | | | |
| | Day 0 | Day 55 | Day 0 | Day 55 | Day 0 | Day 55 |
| Mean worm mass (g) ± standard deviation | 0.8 ± 0.4 | 1.9 ± 0.6 | 0.7 ± 0.2 | 4.2 ± 1.0 | 0.7 ± 0.3 | 4.5 ± 1.3 |
| Worm size range (g) | 0.2 to 1.6 | 0.8 to 3.3 | 0.2 to 1.1 | 2.4 to 6.9 | 0.1 to 1.4 | 2.0 to 8.0 |
| Survival rate (%) | | 95.6 | | 88.9 | | 93.3 |
| Biomass g m$^{-2}$ | 86.9 | 211.5 | 76.2 | 430.8 | 80.0 | 480.8 |
| Mean daily growth increment per worm | | 0.02 | | 0.06 | | 0.07 |

Example 5

In this embodiment of the invention small lugworms obtained by breeding from worms that had been produced and reared as described within this Application were stocked matter already present in the used sand substrate, and that an additional enrichment of sand with fish farm by-product and a mixture of fish farm by-product and brewery yeast significantly enhances the potential for growth of these marine polychaetes.

TABLE 4

| | FOOD STUFF | | | | | | | |
|---|---|---|---|---|---|---|---|---|
| | CONTROL | | BREWERY YEAST | | FISH WASTE | | FISH WASTE/BREWERY YEAST | |
| | | | | TIME | | | | |
| | Day 0 | Day 60 | Day 0 | Day 60 | Day 0 | Day 60 | Day 0 | Day 60 |
| Mean worm mass (g) ± standard deviation | 0.9 ± 0.6 | 2.2 ± 0.8 | 0.9 ± 0.6 | 3.9 ± 1.5 | 0.9 ± 0.5 | 3.5 ± 1.0 | 1.0 ± 0.5 | 5.1 ± 1.1 |
| Worm size range (g) | 0.1–2.0 | 0.7–3.9 | 0.1–2.6 | 1.8–7.5 | 0.1–2.4 | 1.4–5.2 | 0.3–2.1 | 3.9–7.1 |
| Survival rate (%) | | 80.0 | | 45.0 | | 91.7 | | 55.0 |
| Biomass g · m$^{-2}$ | 145.4 | 272.3 | 144.6 | 271.5 | 137.7 | 491.5 | 149.2 | 429.2 |
| Mean daily growth increment per worm | | 0.02 | | 0.05 | | 0.07 | | 0.07 |

Example 6

In this example the fatty acid composition of mature and immature specimens of *Arenicola marina* fed on a number of different diets was determined to find out whether cultured lugworms may be an alternative source of food in the aquaculture industry.

Figure 8:
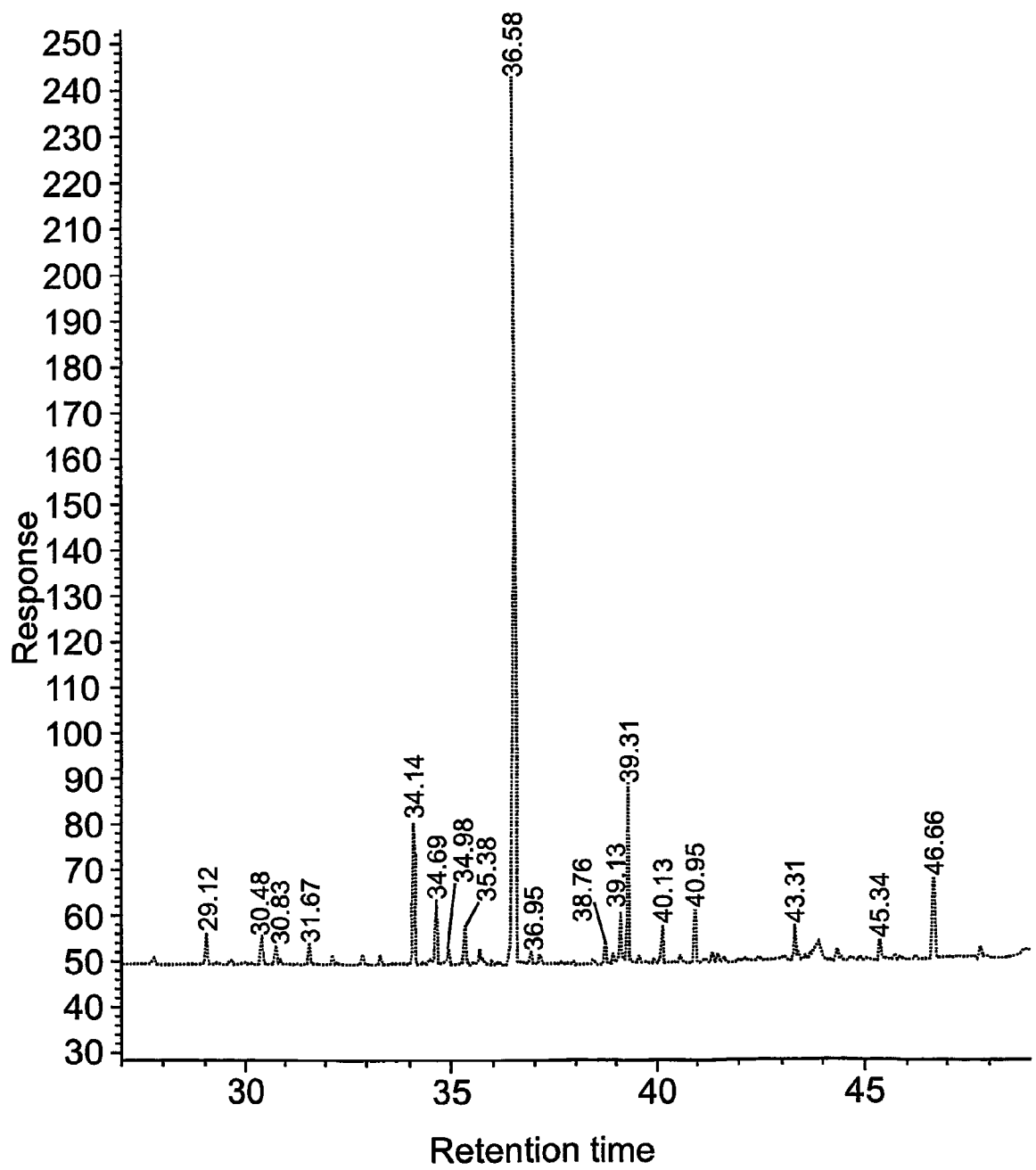
FIG. 8 is a typical chromatograph of somatic tissues of mature *Arenicola marina* [RT=36.58 (C:17), RT=39.13 (SA), RT=40.13/40.95 (LA), RT=41.38 (LNA), RT=45.34 (AA), RT=46.66 (EPA), RT=55.62 (DHA)].
Figure 9:
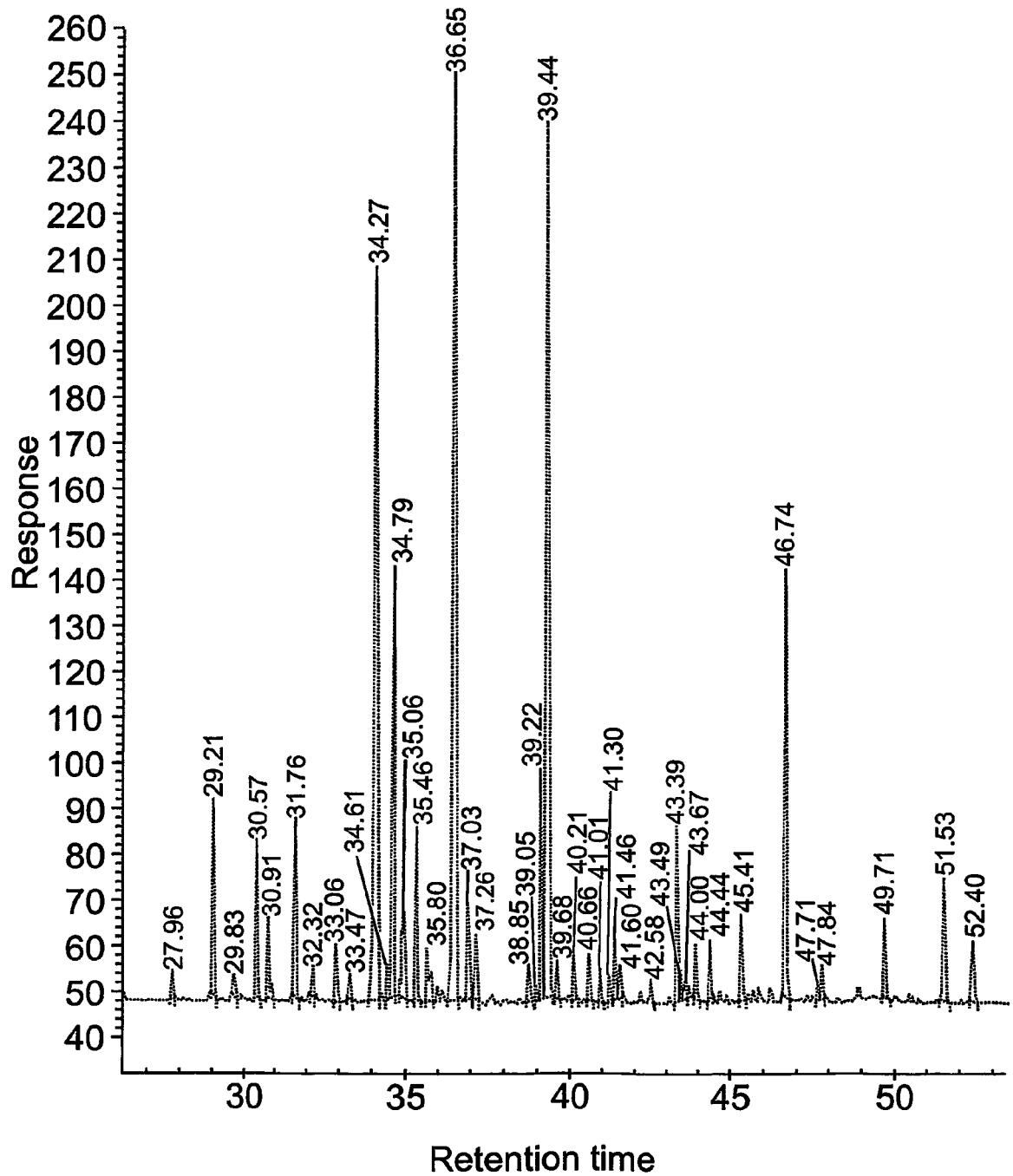
FIG. 9 is a typical chromatograph of gonadal tissues of mature *Arenicola marina* [RT=36.56 (C:17), RT=38.85 (SA), RT=40.21/40.66 (LA), RT=41.46 (LNA), RT=45.41 (AA), RT=46.74 (EPA), RT=52.40 (DHA)].
Figure 10:
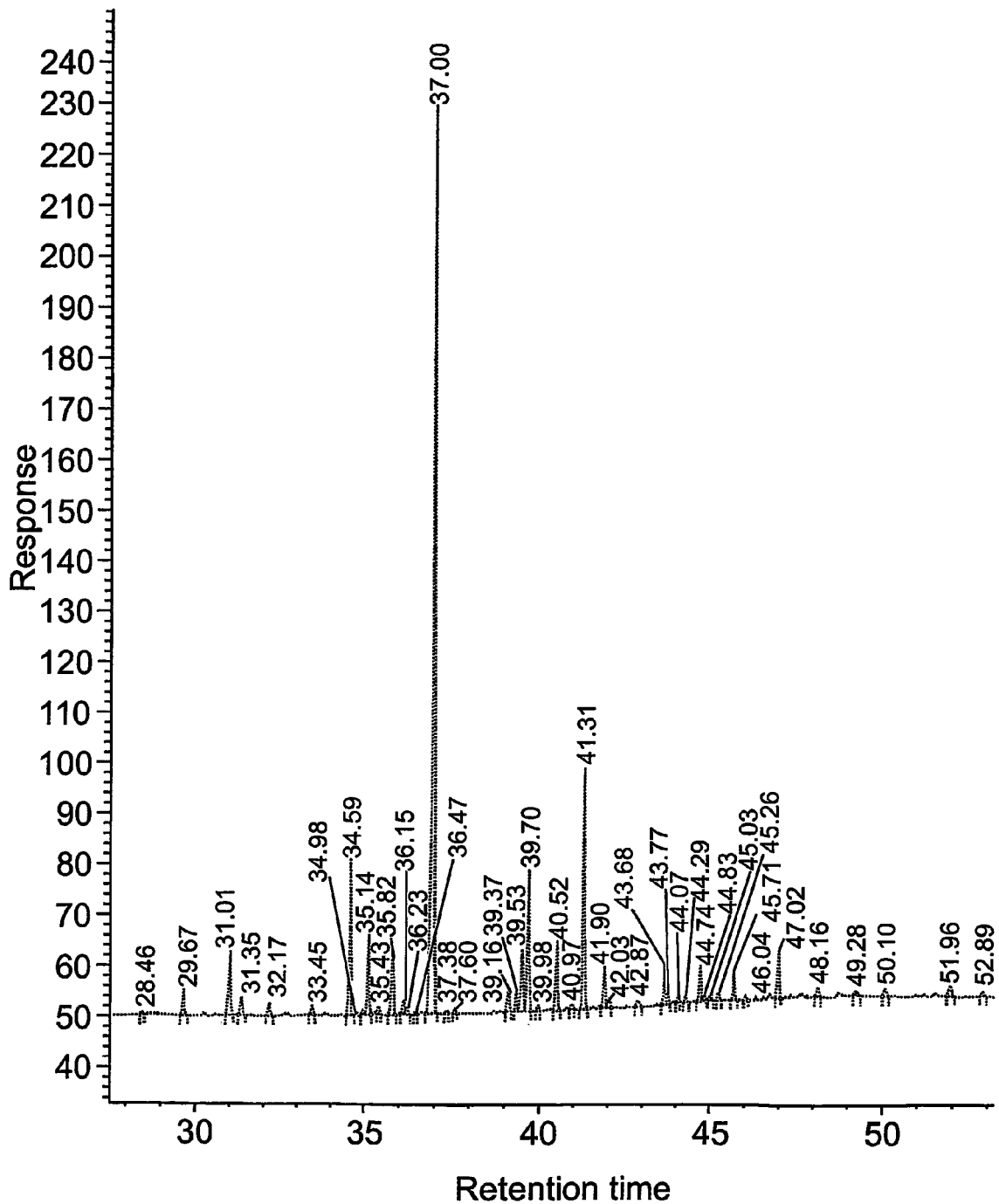
FIG. 10 is a typical chromatograph of immature tissues of *Arenicola marina* fed the brewery yeast diet [RT=37.00 (C:17), RT=39.16 (SA), RT=40.52(LA), RT=41.90 (LNA), RT=45.71 (11), RT=52.89 (DHA).
Figure 11:
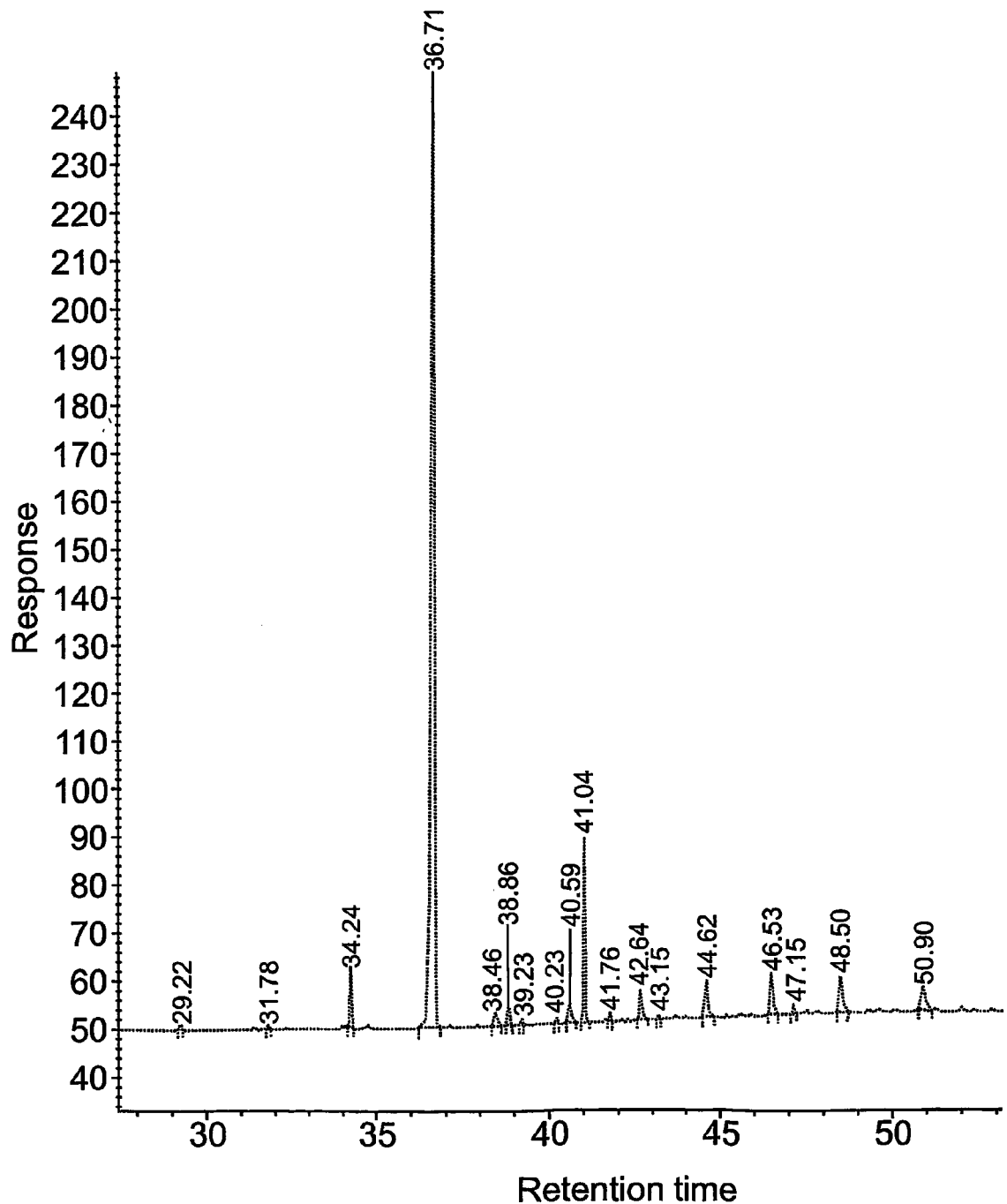
FIG. 11 is a typical chromatograph of brewery yeast feed [RT=36.71 (C:17), RT=38.46 (C24:0), RT=38.86 (SA), RT=44.62 (C27:0), RT=46.53 (C28:0), RT=47.15 (C22:0), RT=48.5 (C29:0) RT=50.9 (C30:0).

The example looked at the concentration of total lipid and total lipid and the total fatty acids analysed as Fatty Acid methyl Esters and partioning and partitioning of these between somatic and gonadal tissue in mature animals. Body tissues of immature animals fed as larvae prior to reaching a weight of 0.1 g on a commercial fish food and then as described in this invention according to Example 1 on brewer's spent yeast have been analysed. A typical GC chromatograph of somatic and gonadal tissue of wild type mature animals are shown in FIGS. 8 and 9 and the body tissue of immature worms fed the diet of brewer's yeast is in FIG. 10. A GC chromatograph of the brewer's yeast obtained from GC is shown in FIG. 11.

The total lipid concentration in the body and gonadal tissues of the native animals (collected from wild populations in the UK, mature animals) and the cultured immature animals fed on brewery waste according to the method in FIG. 1 are given in Table 5.

Table 5 shows the compartmentalisation of total lipid content as % lipid and as mg $g^{-1}$ dry weight in the somatic and gonadal tissues of mature animals collected from the wild and in the combined whole body tissues of animals cultured according to the method described in Example 3 using brewery yeast as the only food source.

TABLE 5

| Sample Types | % Lipid conc. | Lipid in mg $g^{-1}$ dry weight |
|---|---|---|
| Body tissues of mature animals | 7.19 | 71.90 |
| Gonadal tissues of mature animals | 31.41 | 314.1 |
| Body tissues of cultured immature animals fed the brewery yeast diet | 12.62 | 126.2 |
| Brewery yeast diet | 3.25 | 32.5 |

It was found that during the final period of maturation most of the lipid was transferred from the body tissue (71.9 mg $g^{-1}$ DW) to gonadal tissue (314.1 mg $g^{-1}$ DW). It is striking that the animals fed initially as larvae with fish food but then with brewery yeast had a lipid content (126.2 mg $g^{-1}$ DW) that was much higher than that of the brewery yeast food (32.5 mg $g^{-1}$ DW).

The fatty acids present in the total lipid extracted from the somatic and gonadal tissues of lugworms collected from the wild were analysed for the purposes of comparison with the fatty acids present in the total lipid extracted from animals that had been cultured on the brewery yeast food according to the methods described. The fatty acid content (FAMEs mg $g^{-1}$ dry weight) of somatic tissue of mature *Arenicola marina* is summarised in Table 6 and the fatty acid content (FAMEs mg $g^{-1}$ dry weight) of the gonadal tissues of the same animals is summarised in Table 7. This data may be compared with the analysis of the fatty acid content of *Arenicola marina* fed entirely on the brewery yeast food in Table 8. The fatty acid content of the brewery yeast food is summarised in Table 9. The cultured animals (Table 8) had been reared for a period of 90 days on the brewery waste food after having been introduced to the sand/brewery waste mixture as larvae with a weight less than 0.1 g. These cultured worms were not at a sufficient state of sexual maturity to separate and analyse the somatic and gonadal tissues separately. The range of fatty acids is the same in the cultured animals grown on the yeast food as in wild collected worms and include the following fatty acids in substantial amounts: C16:0, C16:1, C18:0, C88:1n12, C18:1n9, C18:1n6/7, C18:2n6, C18:3n3, C20:0, C20:1n9, C20:2n6, C20:4n6, C20:5n3, C22:2n3, C22:6n6 and C22:6n3. It is evident that the fatty acids found in the lipids of the worms grown on the brewery yeast are of substantially the same species as those present in wild type worms including many unsaturated fatty acids that are valued in aquaculture feeds. These fatty acids have accumulated in the tissues of the cultured worms despite the cultured worms having been provided with brewery yeast as the only food source in which the lipid was comprised chiefly of the saturated fatty acids C16:0, C18:0, C22:0, C24:0 C25:0 C26:0 C27:0, C28:0, C29:0, C30:0 and C31:0 all of which were present at amounts greater than 0.4 mg $g^{-1}$ and containing only one unsaturated fatty acid C18:1 present only in small amounts (0.08 mg $g^{-1}$). The biomass accumulated by the lugworms was derived from the brewery yeast as indicated by the very low growth rate of control worms not provided with yeast as shown in FIG. 6. It follows that the lipids were accumulated by the lugworm from this raw material. It is possible however that this diet is not ingested directly but that it undergoes some changes in the culture tanks before being incorporated into lugworm tissues. This process may involve bacterial action on the supplied food.

The data presented in Tables 6 and 7 show that some re-allocation of lipid material from the somatic tissues to the gonadal tissues occurs during sexual maturation of lugworms. For the purposes of providing a convenient nutrient source for aquaculture hatcheries and for providing a convenient and attractive bait it is desirable to harvest the cultured lugworms before this process has taken place in order to minimise the possible loss of lipid by the leakage of the developing eggs or sperm from the worms after they have been harvested. This is achieved by harvesting the worms before they have completed the phase sexual maturation This may be conveniently achieved by harvesting the worms approximately 90 days or less after introduction to the culture system as larvae or juvenile worms. The results presented in Table 10 show that when harvested in this way the cultured animal tissues exhibit a very good fatty acid profile in relation to known hatchery requirements (Table 10).

TABLE 6

Fatty acid content of somatic tissue of mature *Arenicola marina*.

| Peak No. | RT | Systematic name | Nomenclature | Common Name | mg $g^{-1}$ DW |
|---|---|---|---|---|---|
| 1 | 34.14 | Hexadecanoic acid | C16:0 | Palmitic | 4.04 |
| 2 | 34.69 | cis-9-hexadecenoic acid | C16:1n7 | Palmitoleic | 1.90 |
| 3 | 36.58 | Heptadecanoic acid | C17:0 | Margaric | — |
| 4 | 38.76 | Octadecanoic acid | C18:0 | Stearic | 0.63 |
| 5 | 38.96 | 6-octadecenoic acid | C18:1n12 | Petroselenic | 0.27 |
| 6 | 39.13 | 9-octadecenoic acid | C18:1n9 | Oleic | 1.43 |
| 7 | 39.31 | 11/12-octadecenoic acid | C18:1n6/7 | Cis-vaccenic? | 5.45 |

TABLE 6-continued

Fatty acid content of somatic tissue of mature *Arenicola marina*.

| Peak No. | RT | Systematic name | Nomenclature | Common Name | mg g⁻¹ DW |
|---|---|---|---|---|---|
| 8 | 40.13 | 9,12-octadecadienoic acid | C18:2n6 | Linoleic | 1.12 |
| 9 | 40.95 | 9,12-octadecadienoic acid | C18:2n6 | Linoleic | 1.38 |
| 10 | 41.38 | 9,12,15-octadecatrienoic acid | C18:3n3 | Linolenic | 0.23 |
| 11 | 43.31 | 11-eicosenoic acid | C20:1n9 | Gondoic | 1.23 |
| 12 | 45.34 | 5,8,11,14-eicosatetraenoic acid | C20:4n6 | Arachidonic | 0.60 |
| 13 | 46.66 | 5,8,11,14,17-eicosapentaenoic acid | C20:5n3 | EPA | 2.35 |
| 14 | 47.77 | | C22:2n3 | | 0.25 |
| 15 | 55.62 | 4,7,10,13,16,19-docosahexaenoic acid | C22:6n3 | DHA | 0.62 |

TABLE 7

Fatty acid content of the gonadal tissue of *Arenicola marina*.

| Peak No. | RT | Systematic name | Nomenclature | Common Name | mg g⁻¹ DW |
|---|---|---|---|---|---|
| 1 | 34.27 | Hexadecanoic acid | C16:0 | Palmitic | 43.88 |
| 2 | 34.79 | cis-9-hexadecenoic acid | C16:1n7 | Palmitoleic | 22.68 |
| 3 | 35.46 | cis-9-hexadecenoic acid | C16:1n7 | Palmitoleic | 8.20 |
| 4 | 36.65 | Heptadecanoic acid | C17:0 | Margaric | |
| 5 | 38.85 | Octadecanoic acid | C18:0 | Stearic | 2.0 |
| 6 | 39.05 | 6-octadecenoic acid | C18:1n12 | Petroselenic | 0.95 |
| 7 | 39.22 | 9-octadecenoic acid | C18:1n9 | Oleic acid | 13.61 |
| 8 | 39.44 | 11/12-octadecenoic acid | C18:1n6/7 | Cis-vaccenic? | 52.59 |
| 9 | 39.68 | | C18:2n5 | | 1.86 |
| 10 | 40.21 | 10,13-octadecadienoic acid | C18:2n6 | Linoleic | 2.35 |
| 11 | 40.66 | 9,12-octadecadienoic acid | C18:2n6 | Linoleic | 2.41 |
| 12 | 41.46 | 9,12-octadecadienoic acid | C18:3n3 | Linolenic | 2.80 |
| 13 | 43.39 | 11-eicosenoic acid | C20:1n9 | | 8.54 |
| 14 | 45.41 | 5,8,11,14-eicosatetraenoic acid | C20:4n6 | Arachidonic | 4.60 |
| 15 | 46.74 | 5,8,11,14,17-eicosapentaenoic acid | C20:5n3 | EPA | 21.46 |
| 16 | 47.84 | | C22:2n3 | | 1.94 |
| 17 | 51.53 | | C22:6n6 | | 9.16 |
| 18 | 52.40 | 4,7,10,13,16,19-docosahexaenoic acid | C22:6n3 | DHA | 5.09 |

TABLE 8

Fatty acid content of *Arenicola marina* fed the brewery yeast food.

| Peak No. | RT | Systematic name | Nomenclature | Common Name | mg g⁻¹ DW |
|---|---|---|---|---|---|
| 1 | 31.01 | Pentadecacenoic acid | C15:0 | | 3.10 |
| 2 | 34.59 | Hexadecanoic acid | C16:0 | Palmitic | 8.13 |
| 3 | 35.14 | cis-9-hexadecenoic acid | C16:1n7 | Palmitoleic | 3.91 |
| 4 | 37.00 | Heptadecanoic acid | C17:0 | Margaric | |
| 5 | 39.16 | Octadecanoic acid | C18:0 | Stearic | 1.23 |
| 6 | 39.37 | 6-octadecenoic acid | C18:1n12 | Petroselenic | 1.09 |
| 7 | 39.53 | 9-octadecenoic acid | C18:1n9 | Oleic | 3.50 |
| 8 | 39.70 | 11/12-octadecenoic acid | C18:1n6/7 | Cis-vaccenic? | 7.64 |
| 9 | 40.52 | 9,12-octadecadienoic acid | C18:2n6 | Linoleic | 3.47 |
| 10 | 41.90 | 9,12,15-octadecatrienoic acid | C18:3n3 | Linolenic | 2.01 |
| 11 | 43.68 | Eicosanoic acid | C20:0 | Arachidic | 2.14 |
| 12 | 44.07 | 11-eicosenoic acid | C20:1n9 | Gondoic | 0.32 |
| 13 | 44.29 | 11-eicosenoic acid | C20:1n9 | Gondoic | 0.31 |
| 14 | 44.74 | 11,13 eicosadienoic acid | C20:2n6 | eicosadienoic | 2.0 |
| 15 | 45.26 | 11,13 eicosadienoic acid | C20:2n6 | eicosadienoic | 0.40 |
| 16 | 45.71 | 5,8,11,14-eicosatetraenoic acid | C20:4n6 | Arachidonic | 1.43 |
| 17 | 47.02 | 5,8,11,14,17-eicosapentaenoic acid | C20:5n3 | EPA | 2.34 |
| 18 | 48.16 | | C22:2n3 | | 0.48 |
| 19 | 51.96 | | C22:6n6 | | 0.65 |
| 20 | 52.89 | 4,7,10,13,16,19-docosahexaenoic acid | C22:6n3 | DHA | 0.27 |

TABLE 9

Fatty acid content of the brewery yeast food.

| Peak No. | RT | Systematic name | Nomenclature | Common Name | mg g⁻¹ DW |
|---|---|---|---|---|---|
| 1 | 31.78 | Pentadecanoic acid | C15:0 | | 0.04 |
| 2 | 34.24 | Hexadecanoic acid | C16:0 | Palmitic acid | 1.19 |
| 3 | 36.71 | Heptadecanoic acid | C17:0 | Margaric | |
| 4 | 38.46 | Tetracosanoic | C24:0 | Lignoceric | 0.42 |
| 5 | 38.86 | Octadecanoic acid | C18:0 | Stearic acid | 0.40 |
| 6 | 39.23 | 9,octadecenoic acid | C18:1n9 | Oleic | 0.08 |
| 7 | 40.59 | | C25:0 | Pentacosane | 0.64 |
| 8 | 42.64 | Hexacosanoic acid | C26:0 | Cerotic acid | 0.94 |
| 9 | 44.62 | | C27:0 | Heptacosane | 1.12 |
| 10 | 46.53 | | C28:0 | Octacosane | 1.23 |
| 11 | 47.15 | Docosenoic | C22:0 | Behenic | 0.18 |
| 12 | 48.50 | | C29:0 | | 1.20 |
| 13 | 50.90 | | C30:0 | | 0.92 |
| 14 | 53.91 | | C31:0 | | 0.66 |

TABLE 10

Total lipid FAMEs concentration of the free fatty acid concentration of body tissue and gonadal tissue of mature animals of A. marina and the animals fed the brewery yeast diet throughout their life.

| Fames | Mature animals of A. marina (mg g$^{-1}$ DW) | | Cultured animals fed diet of brewery yeast (mg g$^{-1}$ DW) |
|---|---|---|---|
| | Body tissue | Gonadal tissue | Body tissue |
| A.ω 3 | | | |
| C18:3n3 | 0.23 | 2.80 | 2.01 |
| C20:5n3 | 2.35 | 21.46 | 2.34 |
| C22:2n3 | 0.25 | 1.94 | 0.48 |
| C22:6n3 | 0.62 | 5.09 | 0.27 |
| Total ω3 | 3.45 | 31.29 | 5.10 |
| B.ω6** | | | |
| C18:2n6 | 2.50 | 4.76 | 3.47 |
| C20:2n6 | — | — | 2.40 |
| C20:4n6 | 0.60 | 4.60 | 1.43 |
| C22:6n6 | | 9.16 | 0.65 |
| Totalω6 | 3.10 | 18.52 | 7.87 |
| ω3:.ω6 | 1.09:1 | 1.69:1 | 0.64:1 |
| DHA/EPA ratio | 0.26:1 | 0.24:1 | 0.12:1 |

**not including C18:1n6/7.

REFERENCES

Boon, J. J., Liefkens, W. L. C., Rijpstra, M., Bass, M., and De Leeuw, J. W. (1978). "Fatty acids of *Desulfovibrio desufurians* as marker molecules in sedentary environments." *Environmental Biogeochemistry and Geomicrobiology*, 1, 355–372.

Cadee, G. C. (1976). "Sediment reworking by *Arenicola marina* on tidal flats in the Dutch Wadden Sea." *Netherlands Journal of Sea Research*, 10, 440–460.

Clark, R. B., and Olive, P. J. W. (1973). "Recent advances in polychaete endocrinology and reproductive biology." *Oceanography and marine biology, annual review*, 11, 176–223.

Fauchald, K., and Jumars, P. A. (1979). "The diet of worms: a study of polychaete feeding guilds." *Oceanography and Marine Biology: Annual Review*, 17, 193–284.

Gambi, M. C., Castelli, A., Giangrande, A., Lanera, P., Prevedelli, D., and Zunarelli-Vandini, R. (1994). "Polychaetes of commercial and applied interst in Italy: an overview." *Memoires de la Musee nationale d' Histoire naturelle*, 162, 593–603.

Grossman, S., and Reichardt, W. (1991). "Impact of *Arenicola marina* on bacteria in intertidal sediments." *Marine Ecology Progress Series*, 77, 85–93.

Hylleberg, J. (1975). "Selective feeding by *Abarenicola pacifica* with notes on *Abarenicola vagabunda* and a concept of gardening in lugworms." *Ophelia*, 14, 113–137.

Jumars, P. A. (1993). "Gourmands of mud: diet selection in marine deposit feeders." Diet Selection: An inter-disciplinary Approach to Foraging Behaviour, R. N. Hughes, ed., Blackwell Scientific, Oxford, 124–156.

Olive, P. J. W. (1993). "Management of the exploitation of the Lugworm *Arenicola marina* and the Ragworm *Nereis virens* (Polychaeta) in conservation areas." *Aquatic Conservation: Marine and Freshwater Ecosystems*, 3(1), 1–24.

Rijken, M. (1979). "Food and food uptake in Arenicola marina." *Netherlands Journal of Sea Research*, 13, 406–421.

Wells, G. P. (1949). "The behaviour of Arenicola marina L. in sand and the role of spontaneous activity cycles." *Journal of the Marine Biological Association of the United Kingdom*, 28, 465–478.

The invention claimed is:

1. A method for the aquaculture of deposit feeding marine worms, said method comprising providing a foodstuff within a substrate housing the worms or their larvae and providing sufficient seawater to cover the substrate.

2. The method as claimed in claim 1 wherein the worms are members of the family Arenicolidae.

3. The method as claimed in claim 1 wherein the worms are members of the Genus Arenicola.

4. The method as claimed in claim 1 wherein the foodstuff is mixed with the substrate prior to the introduction of worms or their larvae.

5. The method as claimed in any one of claims 1 to 4 wherein the foodstuff is added to a layer of substrate and to which worms or their larvae have already been introduced, said added foodstuff being subsequently admixed with the substrate or covered by additional substrate.

6. The method as claimed in claim 1 wherein a solution or dispersion of the foodstuff is introduced into the substrate from a pipe located within or below the substrate.

7. The method as claimed in claim 1 wherein the foodstuff is admixed with the substrate by a plough or similar device that is pulled through or across the substrate.

8. The method as claimed in claim 1 wherein the foodstuff is admixed with the substrate by use of a venturi pump or similar device that uses the mass flow of a sea water and sand mixture to draw in a mixture of sea water and the foodstuff.

9. The method as claimed in claim 1 wherein the foodstuff is any suitable organic material or food processing waste.

10. The method as claimed in claim 9 wherein the foodstuff comprises yeast.

11. The method as claimed in claim 10 wherein the yeast is a by-product of the brewing industry.

12. The method as claimed in claim 9 wherein the foodstuff is a bacteria-containing slurry.

13. The method as claimed in claim 12 wherein the foodstuff is a bacteria-containing slurry recovered from a fish farm.

14. The method as claimed in claim 12 wherein the foodstuff is slurry recovered from a recirculation filter, biofilter or bioreactor.

15. The method as claimed in claim 9 wherein the foodstuff comprises a mixture of brewery yeast and organic material recovered from a fish farm.

16. The method as claimed in claim 9 wherein the foodstuff comprises composted or partially decomposed marine algae or sea grass or a mixture thereof.

17. A method as claimed in claim 1 wherein the temperature is regulated to maximize growth rate and the progress of sexual maturation of the worms.

* * * * *